United States Patent

Clarke

[19]

[11] Patent Number: 5,860,971
[45] Date of Patent: Jan. 19, 1999

[54] THAWING OF CRYOSURGICAL APPARATUS

[75] Inventor: Brian Kevin Roderick Clarke, Oakwood, England

[73] Assignee: Spembly Cryosurgery Limited, Hampshire, England

[21] Appl. No.: 862,542

[22] Filed: May 23, 1997

Related U.S. Application Data

[63] Continuation-in-part of Ser. No. 232,281, May 31, 1994, Pat. No. 5,632,743.

[30] Foreign Application Priority Data

Nov. 5, 1991 [GB] United Kingdom ............... 9423413

[51] Int. Cl.$^6$ .................................................. A61B 17/36
[52] U.S. Cl. .................................. 606/24; 606/20; 606/22; 606/23
[58] Field of Search .................. 606/20–26; 62/512, 62/293

[56] References Cited

U.S. PATENT DOCUMENTS

| | | | |
|---|---|---|---|
| Re. 28,657 | 12/1975 | Barger et al. | 606/23 |
| 3,613,689 | 10/1971 | Crump et al. | 606/23 |
| 3,913,581 | 10/1975 | Ritson et al. | 606/23 |
| 3,993,075 | 11/1976 | Lisenbee et al. | 62/293 |
| 4,018,227 | 4/1977 | Wallach | 128/303.1 |
| 4,063,560 | 12/1977 | Thomas et al. | 128/303.1 |
| 4,206,760 | 6/1980 | Davis | 128/303.1 |
| 4,275,734 | 6/1981 | Mitchiner | 128/303.1 |
| 4,278,090 | 7/1981 | van Gerven | 128/303.1 |
| 4,280,499 | 7/1981 | Squazzi | 128/303.1 |
| 4,348,873 | 9/1982 | Yamauchi | 606/20 X |
| 4,377,168 | 3/1983 | Rzasa et al. | 128/303.1 |
| 4,519,389 | 5/1985 | Gudkin et al. | 128/303.1 |
| 4,946,460 | 8/1990 | Merry et al. | 606/24 |
| 5,108,390 | 4/1992 | Potocky et al. | 606/21 |
| 5,224,943 | 7/1993 | Goddard | 606/20 |

FOREIGN PATENT DOCUMENTS

| | | | |
|---|---|---|---|
| 86-086863/14 | 6/1983 | U.S.S.R. | A61B 17/36 |
| 86-296896/45 | 3/1986 | U.S.S.R. | A61B 17/36 |
| WO 83/03861 | 11/1983 | WIPO | A61F 7/00 |

*Primary Examiner*—Michael Buiz
*Assistant Examiner*—Julian W. Woo
*Attorney, Agent, or Firm*—Adams Law Firm, P.A.

[57] ABSTRACT

Apparatus is described for feeding a cryosurgical device by passing a liquid cryogen (e.g. liquid nitrogen) through the device to produce cooling by vaporization, and to enable thawing of the device by passing a heated inert thaw gas (e.g. nitrogen gas) through the device when the liquid cryogen is turned off. The thaw gas is passed through the device in the same direction of flow as the liquid cryogen. The apparatus can supply a plurality of cryosurgical devices, and provide independent control of cryogen and thaw for each probe. Novel valve arrangements are also disclosed for controlling the supply of liquid cryogen and the supply of the thaw gas.

19 Claims, 3 Drawing Sheets

THAWING OF CRYOSURGICAL APPARATUS

This is a continuation-in-part of application No. 08/232,281 filed on May 31, 1994, which is now U.S. Pat. No. 5,632,743; which is a continuation of PCT pub. No. WO93/08752, dated May 13, 1993.

FIELD OF THE INVENTION

The invention concerns cryosurgical apparatus, and relates in particular to a technique for thawing a cryosurgical probe subsequent to carrying out a freezing process, in order that the probe may be withdrawn.

DISCUSSION OF BACKGROUND ART

Following an operation involving the destruction of tumorous tissue by freezing with a cooled probe inserted into the body, it is necessary to thaw or allow to be thawed the tissue immediately surrounding the probe in order that the latter may be withdrawn. Such thawing is commonly carried out by one of two principal methods. The first involves the use of latent body heat. This has the serious disadvantage that the process is extremely slow, thereby significantly increasing operation times. The second method utilises electrical heating of the probe tip. Although this is a considerably faster method, there are inherent safety problems which necessitate the utmost care in producing and using equipment of this kind.

OBJECT OF THE INVENTION

This invention seeks to mitigate or obviate the above mentioned difficulties by providing a relatively fast yet safe technique for raising the temperature of the probe tip on completion of an operation.

SUMMARY OF THE INVENTION

In one aspect, the invention provides cryosurgical apparatus comprising:

a cryosurgical device having a tip region and a liquid cryogen pathway for transporting liquid cryogen through the tip region to cool the tip region by vaporisation of the cryogen, the pathway including an inlet and an outlet;

a liquid cryogen supply coupled to said inlet for selectively supplying liquid cryogen through the inlet in order to produce said cooling at said tip region;

an inert gas supply coupled to said inlet for selectively supplying an inert thaw gas after said supply of cryogen has been stopped at the end of surgery, to thaw the cryosurgical device; and an exhaust line coupled to said outlet of said pathway of said cryosurgical device.

This technique is particularly suited to liquid nitrogen cooled probes, such as the kind in which the cryogen is delivered to the probe tip via a delivery tube located along the probe axis and returned via an annular gap within the probe housing surrounding the delivery tube.

Preferably the inert gas is nitrogen. The gas may be heated by feeding it to the apparatus via a heat exchanging arrangement.

In a closely related aspect, the invention provides apparatus for supplying liquid cryogen and heated thaw gas to a cryosurgical device of a type having a tip region and a pathway for transporting liquid cryogen through the tip region to cool the tip region by vaporization of the cryogen, the pathway having an inlet and an outlet, wherein said apparatus comprises:

a first conduit for coupling to said inlet of said pathway of the cryosurgical device;

a second conduit for coupling to said outlet of the cryosurgical device;

a cryogen delivery control valve;

a liquid cryogen supply coupled to said first conduit, to selectively supply liquid cryogen to the cryosurgical device under the control of said cryogen delivery control valve;

a gas delivery control valve:

an inert gas supply coupled to said first conduit, to selectively supply under the control of said gas delivery control valve a thaw gas to thaw the cryosurgical device after the supply of cryogen has been stopped at the end of surgery, whereby said apparatus is operable to supply said liquid cryogen and thereafter said thaw gas through said inlet conduit.

The cryogen delivery control valve may be coupled between the cryogen supply and the first conduit. Such a valve would then have to be capable of withstanding and operating at cryogenic temperatures. An alternative is to use a gas pressure control valve to control the pressure of propellant gas acting on the liquid cryogen; the rate of flow of cryogen can then be controlled indirectly by varying the propelling pressure within the cryogen supply. Such a technique is described in the inventor's published International patent application WOA-96/30816, the content of which is incorporated herein by reference. The advantage of that arrangement is that the cryogen delivery control valve does not have to be placed in the cryogen flow path.

The gas delivery control valve for the thaw gas may be located between the inert gas supply and the inlet of the cryosurgical device, or it may be located within the gas supply system, for example as an inline valve.

In a further related aspect, the invention provides cryosurgical apparatus comprising:

a first cryosurgical device having a first tip region and a first liquid cryogen pathway for transporting liquid cryogen through the tip region to cool the tip region by vaporization of the cryogen, the pathway including a first inlet and a first outlet;

a second cryosurgical device having a second tip region and a second cryogen pathway for transporting liquid cryogen through the tip region to cool the tip region by vaporization of the cryogen, the pathway including a second inlet and a second outlet;

a liquid cryogen supply system;

a first cryogen delivery valve for controlling the supply of liquid cryogen to the first cryosurgical device;

a second cryogen delivery valve for controlling the supply of liquid cryogen to the second cryosurgical device;

an inert gas supply for supplying thaw gas;

a fit thaw gas delivery valve for controlling the supply of thaw gas to thaw the first cryosurgical device after the first cryogen delivery valve has been turned off; and a second thaw gas delivery valve for controlling the supply of thaw gas to thaw the second cryosurgical device after the second cryogen delivery valve has been turned off.

In a further aspect, the invention provides a method of thawing cryosurgical apparatus having an internal circulation system for fluid cryogen, which method comprises the steps of interrupting a supply of the cryogen to the apparatus, providing a supply of an inert gas, heating the gas to a required predetermined temperature, and circulating the heated gas through the cryogen circulation system of the apparatus to effect the required thawing.

BRIEF DESCRIPTION OF THE DRAWINGS

Embodiments of the invention are described below by way of example only, with reference to the accompanying drawings, in which.

DESCRIPTION OF PREFERRED EMBODIMENTS

Figure 1:
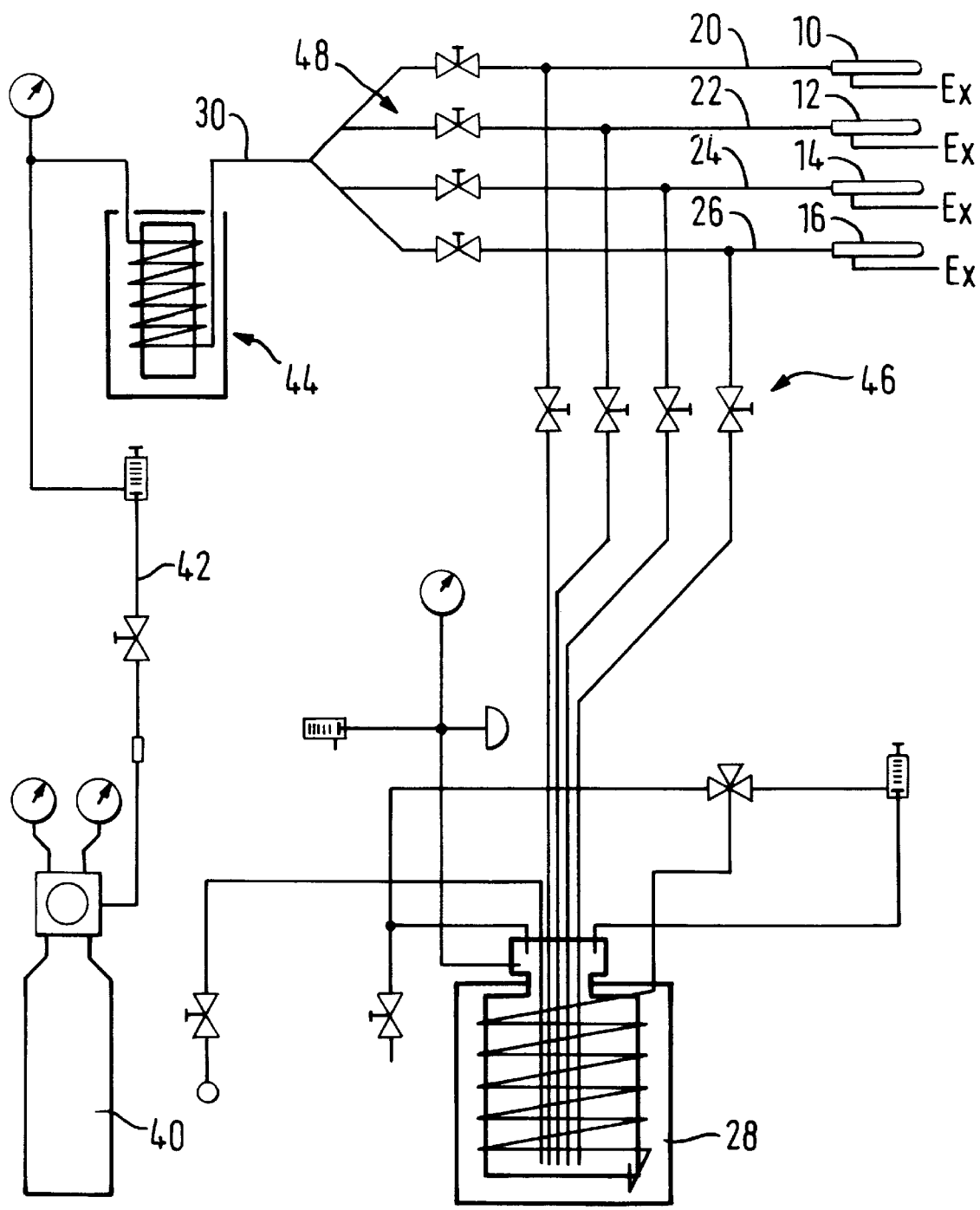
FIG. 1 is a schematic block diagram showing a cryosurgical probe arrangement for utilising the thawing technique, of the invention.

FIG. 1 shows an arrangement containing four cryosurgical probes 10, 12, 14 and 16. Each probe Is connected by a delivery line 20, 22, 24 and 26 to a supply vessel 28 of a fluid cryogen, such as liquid nitrogen.

The lines 20, 22, 24 and 26 are also in communication with a further delivery line 30 as described in more detail hereinafter.

The system provides a supply 40 of an inert gas, in the present example, nitrogen. Gas may be supplied through a delivery line 42 to a heat exchanging arrangement 44, and thus to the cryogen circulation systems of the probes 10, 12, 14 and 16 via the line 30 and the lines 20, 22, 24 and 26.

Each of the probes 10, 12, 14 and 16 may be supplied with the cryogen from the supply vessel 28 in any convenient manner, such as via a delivery tube located along the respective probe longitudinal axis, as is well known in the art. Following vaporization of the liquid cryogen at the probe tip, the cryogen is then removed, for example via an annular gap within a housing of the probe surrounding the delivery tube, to a suitable exhaust line on the probe.

When the operation is complete and it is required to withdraw the probe, the supply of cryogen from the vessel 28 Is shut off by means of a suitable valve a arrangement 46. Gas is passed from the supply 40 through the line 42 to the heat exchanger 44. On passing through the heat exchanger, the gas is warmed to the required predetermined temperature. From the heat exchanger 44 the gas supply is passed through the line 30 and then via suitable valve systems 48 to the supply line of the appropriate probe, The warmed nitrogen is thereby circulated through the probe body and tip whereby it provides localized heat within the probe tip. The gas may then be exhausted through the existing probe cryogen outlet lines.

Any cryogen remaining within the probe circulation system is automatically purged by the incoming gas supply.

It will be appreciated that control and monitoring of the apparatus can be achieved by the incorporation of any appropriate valves, gauges, regulators or other instrumentation as is well known to the person skilled in the art. Such systems are not therefore described in detail herein.

There is therefore described a particularly convenient way of raising the temperature of the probe body. The method naturally permits suitable control of the speed of the thawing process by appropriate adjustments to the gas supply. The use of nitrogen gas in the given example also obviates problems of the formation of ice deposits within the cryogen circulation system on re-cooling which could arise if, for example, a liquid was used as the purging and heat transfer medium.

The further embodiments described below operate in a similar manner to that described above, but use a different technique for controlling the delivery of the liquid cryogen. This technique is described in the inventor's published International patent application WO-A-96/30816 (incorporated above) to which the reader is referred for fiber information. To illustrate the principles, FIG. 2 illustrates a second relatively simple embodiment for driving a single cryosurgical probe 10.

Figure 2:
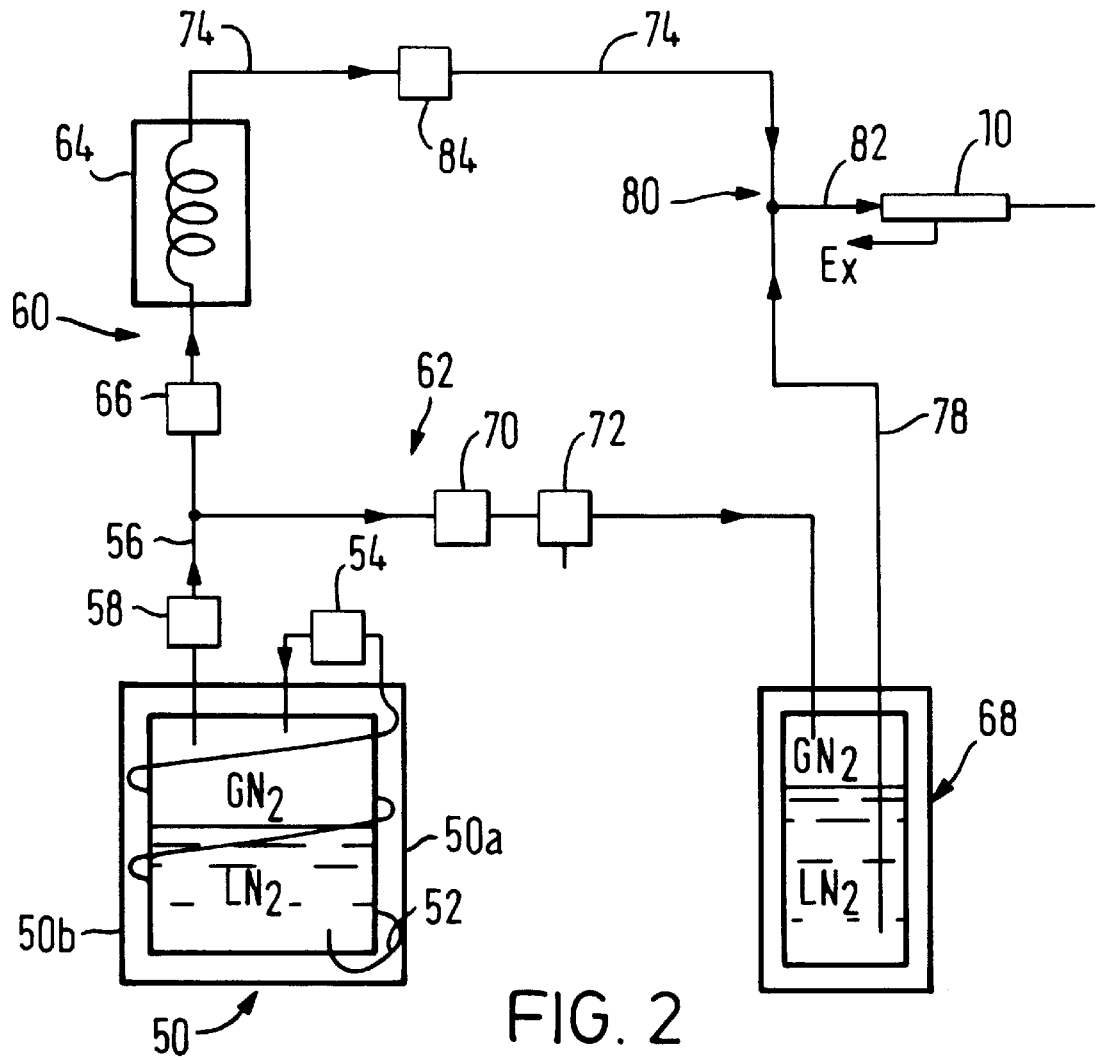
FIG. 2 is a schematic block diagram showing a second embodiment of the invention.

Referring to FIG. 2, the system includes a pressure raising vessel 50 containing liquid nitrogen. The vessel 50 is very similar to the vessel 28 illustrated in FIG. 1, but is used to provide a source of pressurized nitrogen gas, rather than a source of liquid cryogen. The pressure raiser 50 includes an outer vessel 50a surrounding an inner vessel 50b which is part filled with liquid nitrogen. A heat exchange conduit 52 is carried on the inner face of the outer vessel 50b to be in the contact with the surroundings. The heat exchange conduit 52 is joined at its lower end to a port at the bottom of the inner vessel 50b to allow liquid nitrogen to flow into the conduit 52. At its upper end, the heat exchanger conduit is coupled through a pressure regulator 54 to a port at the upper end of the inner vessel 52. In use, liquid cryogen enters the evaporation conduit 52 at the bottom, and evaporates by absorption of heat through the wall of the outer vessel 50a. The gas then passes through the regulator 54 under pressure and renters the inner vessel 50b at the top. Very quickly, a head of gaseous pressure will develop in the upper part of the inner vessel 50b. When this pressure reaches the value set by the regulator 54, the flow through the heat exchange conduit 52 will sop will stop since there will be no pressure differential. When gas is drawn away from the pressure raiser 50 through the outlet conduit 56, cryogen will again flow in the heat exchange conduit 52 until the head of pressure is restored to its maximum value set by the regulator 54.

The outlet conduit 56 may be coupled through an external pressure regulator 58 as desired. The outlet then branches to two gaseous circuit paths 60 and 62.

The first path 60 is very similar to the thaw gas supply circuit illustrated in FIG. 1. In particular, it includes a heat exchanger 64 for heating the nitrogen gas for use as the thaw gas at a predetermined temperature. A master gas control valve 66 may be provided for controlling the flow of gas into the heat exchanger. A thaw gas delivery control valve 84 is coupled downstream of the heat exchanger.

In the second gas path 62, the nitrogen gas Is used as a propellant for driving liquid cryogen from a reservoir dewer 68. The second path 62 includes a variable valve 70 for enabling the pressure of the gas to be controlled variably, and a shut off/vent valve 72 for selectively (1) passing the gas pressure to the dewer 68, or (2) venting the dewer 68 to atmosphere; or (3) blocking the inlet to the dewer 68 from both the surrounding atmosphere and the pressurised liquid nitrogen gas. Win in position (1), the valve 72 allows the cryogen to be delivered at a rate set by the pressure of the propellant gas. When in position (2), the valve 72 allows the cryogen supply to be stopped immediately, by venting the propellant pressure in the dewer to atmosphere. When in position (3), the valve 72 isolates the dewer 68 so that no further propellant gas can be delivered, and no propellant pressure can escape. This position can be used during the thaw mode, as described further below.

In this embodiment, the thaw gas outlet conduit 74 from the first circuit 60, and the liquid cryogen delivery conduit 78 from the dewer 68 are Joined at a simple T junction 80, which provides a common feed 82 to the let of the cryosurgical probe In use, during freezing, the thaw gas valve 84 is shut off, and the valves 70 and 72 are operated either manually or automatically (for example, by electronic control apparatus as described in WO-A-96/30816) to deliver cryogen at a desired flow rate. Since the valve 84 is turned off, no liquid cryogen will escape into the thaw gas circuit 60, and the cryogen will all be directed into the feed line 82 to the probe 10.

To enable the flow of cryogen to be controlled accurately, it is important that the liquid cryogen contained in the dewer 68 does not itself evaporate to create an "uncontrollable" contribution to the propellant pressure. The dewer 68 is preferably thermally insulated from the ambient temperature surroundings (for example, by being vacuum insulated, or being placed within a further cryogen containing vessel and/or being placed with a vacuum-insulated vessel, as in FIG. 5).

At the end of freezing, the valve 72 is moved to position (2) to vent the pressure within the dewer 68, and hence halt the flow of cryogen.

Thereafter, the thawing cycle can be commenced by opening the thaw gas delivery valve 84 (and the master valve 66 if not already open), to allow the thaw gas to flow from the pressure raiser 50 trough the heat exchanger 64 and through the thaw gas delivery conduit 74. In contrast to the first embodiment, the cryogen delivery conduit 78 does not have a cryogen delivery control valve, and so other techniques must be used to direct the thaw gas to flow predominately into the probe, and to limit the amount of thaw gas leaking along the conduit 78 to the dewer 68*b*. With the present embodiment, this can be accomplished in two ways.

The first is to set the control valve 72 to position (3) to isolate the dewer 68. Initially some thaw gas may flow along the conduit 78 to the dewer 68, and bubble through the liquid cryogen. However, since the dewer 68 is isolated by the valve 72, a back pressure will quickly begin to develop in the dewer 68 and the conduit 78, thus obstructing further flow of thaw gas into the conduit 78. The heat in the thaw gas which does initially enter the dewer 68 may cause a small amount of the liquid nitrogen cryogen to vaporize, but this will only serve to accelerate the development of back pressure with the dewer 68.

The alternative technique is to set the valve 72 to position (1), and to operate control valve 70 to generate a "balancing" back pressure within the dewer 68. This is very similar to the previous technique, except that the back pressure is controlled through the circuit 62 instead of relying on limited wastage of the heated thaw gas. Thus the flow of thaw gas into the probe 10 can be stabilized more quickly.

It will be appreciated that should the thaw gas delivery control valve 84 become frozen shut (which may happen when the valve is in contact with the liquid cryogen during the freezing operation), the valve can thaw automatically when the heated thaw gas flows through the heat exchanger to communicate heat to the valve.

Figure 3:
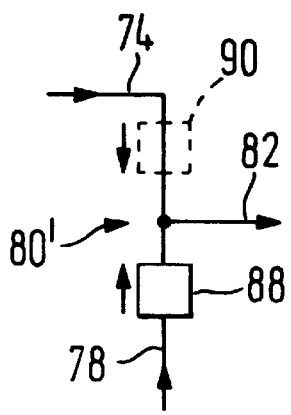
FIG. 3 is a pa schematic block diagram showing a modification of the arrangement of FIG. 2.

FIG. 3 illustrates a modification of the T-junction region 80' of the system. In this modification, a simple non-return (one-way) valve 88 is arranged in the cryogen delivery conduit 78, to allow flow only in the direction indicated by the arrow. The valve 88 prevents thaw gas from leaking into the cryogen conduit 78, and ensures that all of the thaw flows towards the probe 10. Thus, the need to develop a back pressure in the dewer 68 can be avoided, although this facility may be retained in case the non-return valve is prone to leakage.

In contrast to a cryogen delivery control valve in the conduit 78 (for example, a valve 46 as in FIG. 1) which requires external control and represents considerable thermal mass in contact with the cryogen flow path, a non-return valve 88 can be completely self maintained and represent a negligible (or at least a more acceptable) thermal mass. Thus the presence of the non-return valve 88 does not detract from the advantages achieved by omitting a delivery control valve from the cryogen conduit 78.

If desired, a non-return valve 90 (illustrated in phantom In FIG. 3) may be used in the thaw gas delivery conduit 74 to prevent any potential freezing of the gas control valve 84.

Figure 4A:
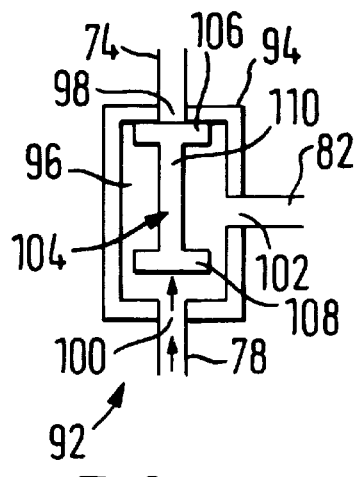
FIGS. 4a and 4b are partial schematic block diagrams showing an alternative modification of the arrangement of FIG. 2.
Figure 4B:
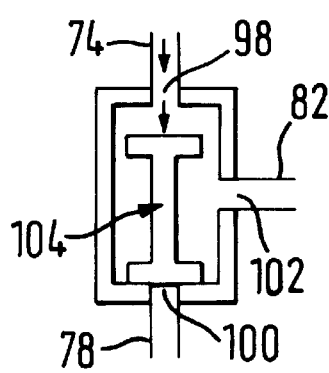

FIGS. 4*a* and 4*b* illustrate a further modification of the T-junction region 80' of the system. In these figures, a self actuating changeover valve 92 replaces the junction and the non-return valve(s). The changeover valve 92 consists of a housing 94 with a chamber 96, and a thaw gas port 98, a cryogen port 100 and an outlet port 102 coupled respectively to the thaw gas conduit 74, the cryogen conduit 78, and the probe feed conduit 82. Within the housing is a slidable slug 104 having enlarged ends 106 and 108 joined by a waist 110. The slug 104 is a very loose fit in the chamber 96, but is constrained to slide generally axially.

In use, when liquid cryogen is supplied under pressure through port 100, and the thaw gas is shut off, the pressure of the cryogen acting on the end face of the slug 104 urges the slug to move away from the port 100 to block the opposite port 98 (see FIG. 4*a*). The cryogen can pass through the circumferential gap between the end 108 and the inside surface of the chamber 96, and around the waist to the outlet port 102. Similarly, the when the liquid cryogen is cut off, and the thaw gas is supplied under pressure, the slug is urged 104 in the opposite direction to block the cryogen port 100, and to leave open a path between the thaw gas port 98 and the outlet port 102.

It will be appreciated that the enlarged ends 106 and 108 do obstruct the flow of gas or liquid cryogen in the chamber 96 to some extent, and this maintains a positive pressure on the slug 104 to block the opposite port. The enlarged end closest to the port through which pressure is being applied can be regarded as acting as a "sail" to drive the slug 104, and the opposite end can be regarded as a seal to block the "passive" port. In either position of the slug 104, neither end 106 or 108 blocks the outlet port 102.

Figure 5:
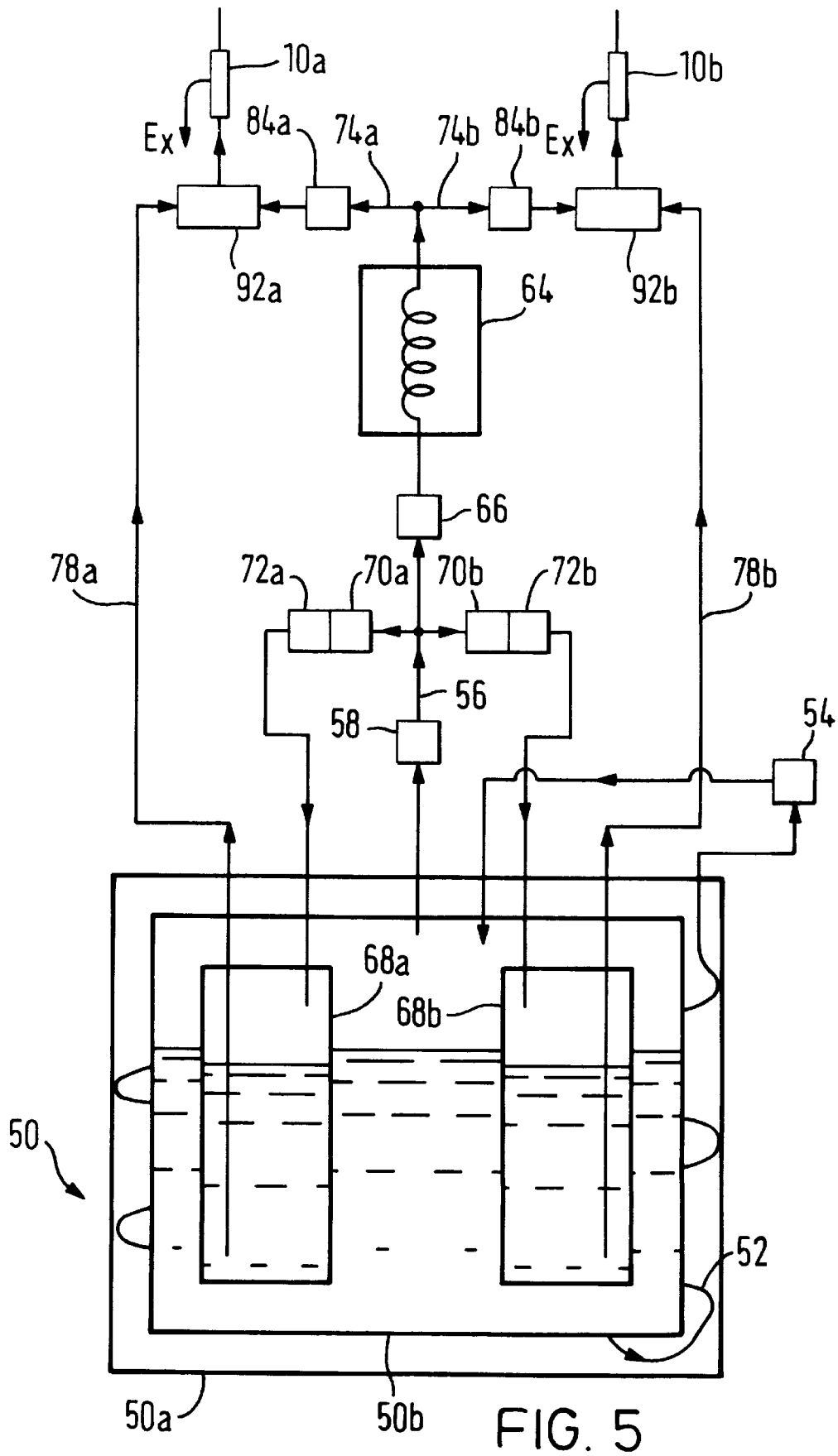
FIG. 5 is a schematic block diagram showing a third embodiment similar to that of FIG. 2.

FIG. 5 illustrates a further embodiment which utilizes the principles of the embodiments of FIGS. 2 to 4, but in a system for supplying liquid cryogen and heated thaw gas to a plurality of probes (two probe "channels" being illustrated) with independent controls for each probe. In FIG. 5 the same reference numerals have been used to denote features described hereinbefore, with suffixes "a" and "b" for each probe channel. In this embodiment, the cryogen dewers 68*a* and 68*b* are mounted within the pressure raiser 50, to exploit the thermal insulation achievable from immersing the dewers 68 within the liquid nitrogen of the inner pressure raising vessel 50*b*, and from the vacuum insulated region between the outer and inner vessels 50*a* and 50*b*. It will be appreciated that this embodiment is not limited only to two supplying two probes, and that additional dewers 68, and valves 84, 70, 72 and 92 may be included to supply more probes in a complete system.

Although the probes 10 in the above embodiments are only illustrated as having a single inlet and a single outlet, this is merely for ease of representation. In particular, it is envisaged that the probes may have two or more outlets, for example, a tip exhaust outlet and a tip bypass outlet as described in commonly owned published patent application WO-A-95/30379, the contents of which are incorporated herein by reference.

It will be appreciated that the invention, particularly as described in the above embodiments, can provide simple yet very effective and-safe thawing of cryosurgical probes, or other cryosurgical devices.

I claim:

1. Cryosurgical apparatus comprising:
   a cryosurgical device having a tip region and a liquid cryogen pathway transporting liquid cryogen through the tip region to cool the tip region by vaporization of the cryogen, the pathway including an inlet and an outlet;
   a liquid cryogen, supply coupled to said liquid cryogen pathway inlet for selectively supplying the liquid cryogen through the inlet in order to produce said cooling at said tip region;
   an inert gas supply coupled to said liquid cryogen pathway inlet for selectively supplying an inert thaw gas after said supply of cryogen has been stopped at the end of surgery, to thaw the cryosurgical device;
   an exhaust line coupled to said outlet of the pathway of said cryosurgical device.

2. Apparatus according to claim 1, wherein said inert gas supply comprise a supply of nitrogen.

3. Apparatus according to claim 1, wherein said inert gas supply comprises a heat exchanger for heating said inert gas.

4. Apparats according to claim 1, wherein said cryosurgical device is a cryosurgical probe with said tip region at a distal end thereof.

5. Apparatus according to claim 4, wherein said pathway comprises a delivery tube coupled between said inlet and said tip region, and an annular return passage coupled between said tip region and said outlet.

6. Apparatus according to claim 11 wherein said liquid cryogen supply comprises a supply of liquid nitrogen.

7. Apparatus for supplying liquid cryogen and heated thaw gas cryosurgical device of a type having a tip region and a pathway for transporting liquid cryogen through the tip region to cool the tip region by vaporization of the cryogen, the pathway having an inlet and an outlet, wherein said apparatus comprises:
   a first conduit for coupling to said liquid cryogen pathway inlet of the cryosurgical device;
   a second conduit for coupling to said liquid cryogen pathway outlet of the cryosurgical device;
   a cryogen delivery control valve;
   a liquid cryogen supply coupled to said first conduit, to selectively supplying liquid cryogen to the cryosurgical device under the control of said cryogen delivery control valve;
   a thaw gas delivery control valve;
   an inert gas supply coupled to said first conduit, to selectively supply under the control of said gas delivery control valve a thaw gas to thaw the cryosurgical device after the supply of cryogen has been stopped at the end of surgery, whereby said apparatus is operable to supply said liquid cryogen and thereafter said thaw gas through said first conduit.

8. Apparatus according to claim 7, wherein said inert gas supply comprises supply of nitrogen.

9. Apparatus according to claim 7, wherein said inert gas supply comprises a heat exchanger for heating said inert gas.

10. Apparatus according to claim 7, wherein said liquid cryogen supply comprises a supply of liquid nitrogen.

11. Apparatus according to claim 7, wherein said cryogen delivery control valve is coupled between said liquid cryogen supply and said first conduit.

12. Apparatus according to claim 7, wherein said liquid cryogen supply comprises a reservoir of liquid cryogen, and said apparatus further comprises a source of propellant gas under pressure to pressurise said reservoir and to drive said cryogen from said reservoir at a rate determined by the pressure of the gas, wherein said cryogen delivery control valve comprises a valve for controlling the pressure of propellant gas supplied to the reservoir.

13. Apparatus according to claim 12, comprising a valve for selectively sealing a gas flow path film the reservoir.

14. Apparatus according to claim 12, comprising a valve for selectively venting a gas path from the reservoir.

15. Apparatus according to claim 12, comprising a one-way valve coupled between said first conduit and said liquid cryogen supply for preventing thaw gas from leaking to the liquid cryogen supply.

16. Apparatus according to claim 12, comprising a changeover valve having a first port coupled to the inert gas supply, a second port coupled to the liquid cryogen supply, and a third port coupled to said first conduit, said changeover valve comprising a valve member movable by pressure differential to selectively block the first port when liquid cryogen is supplied under pressure from the liquid cryogen supply, and to selectively block the second port when thaw gas is supplied under pressure from the inert gas supply.

17. Apparatus according to claim 16, wherein the valve member comprises a slug slidable in a chamber of the changeover valve.

18. Apparatus according to claim 7, wherein the thaw gas delivery control valve is coupled between the first conduit and the inert gas supply.

19. Cryosurgical apparatus comprising:
   first cryosurgical device having a first tip region and a first liquid cryogen pathway for transporting liquid cryogen through the tip region to cool the tip region by vaporization of the cryogen, the pathway including a first inlet and a first outlet;
   a second cryosurgical device having a second tip region and a second cryogen pathway for transporting liquid cryogen through the tip region to cool the tip region by vaporization of the cryogen, the pathway including a second inlet and a second outlet;
   a liquid cryogen supply system;
   a first cryogen delivery valve for controlling the supply of liquid cryogen to the first cryosurgical device;
   a second cryogen delivery valve for controlling the supply of liquid cryogen to the second cryosurgical device;
   an inert gas supply for supplying thaw gas;
   a first thaw gas delivery valve coupled between said inert gas supply and said first liquid cryogen pathway inlet of said first cryosurgical device for controlling the supply of thaw gas to thaw the first cryosurgical device after the first cryogen delivery valve has been turned off; and
   a second thaw gas delivery valve coupled between said inert gas supply and said second liquid cryogen-pathway inlet of said second cryosurgical device for controlling the supply of thaw gas to thaw the second cryosurgical device after the second cryogen delivery valve has been turned off.

* * * * *